(12) United States Patent
Petersen et al.

(10) Patent No.: US 10,273,463 B2
(45) Date of Patent: Apr. 30, 2019

(54) CHEMILUMINESCENT WETNESS INDICATOR FOR ABSORBENT PRODUCTS

(71) Applicant: INTERNATIONAL PAPER COMPANY, Memphis, TN (US)

(72) Inventors: Brent A. Petersen, Tacoma, WA (US); Venketa R. Parthasarathy, Pooler, GA (US)

(73) Assignee: INTERNATIONAL PAPER COMPANY, Memphis, TN (US)

( * ) Notice: Subject to any disclaimer, the term of this patent is extended or adjusted under 35 U.S.C. 154(b) by 988 days.

(21) Appl. No.: 14/516,255

(22) Filed: Oct. 16, 2014

(65) Prior Publication Data

US 2016/0108375 A1 Apr. 21, 2016

(51) Int. Cl.
*A61F 13/15* (2006.01)
*C12N 9/02* (2006.01)
(Continued)

(52) U.S. Cl.
CPC ............ *C12N 9/0069* (2013.01); *A61L 15/28* (2013.01); *A61L 15/40* (2013.01); *A61L 15/56* (2013.01); *C12Y 113/12005* (2013.01); *C12Y 113/12007* (2013.01); *A61F 13/15585* (2013.01); *A61F 13/15617* (2013.01); *A61F 13/49* (2013.01); *A61F 13/51* (2013.01); *A61F 13/513* (2013.01); *A61F 13/5116* (2013.01);
(Continued)

(58) Field of Classification Search
CPC .............. A61F 13/8405; A61F 13/5116; A61F 13/513; A61F 13/51305; A61F 13/49; A61F 13/15585; A61F 13/15617; A61F 13/51; A61F 2013/426; A61F 2013/427; A61F 2013/428; A61F 2013/429; C12N 9/0069; C12Y 113/12007; A61L 15/28; A61L 15/40; A61L 15/56; A61L 2300/30; A61L 2300/442
USPC ................................... 604/361, 362
See application file for complete search history.

(56) References Cited

U.S. PATENT DOCUMENTS 2,681,032 A 6/1954 Shaw
3,675,654 A 7/1972 Baker
(Continued)

FOREIGN PATENT DOCUMENTS

CN 103720539 A 4/2014
EP 0 203 715 B1 3/1991
(Continued)

OTHER PUBLICATIONS

International Preliminary Report on Patentability dated Apr. 27, 2017, issued in corresponding International Application No. PCT/US2015/053400, filed Oct. 1, 2015, 10 pages.
(Continued)

*Primary Examiner* — Jacqueline Stephens
(74) *Attorney, Agent, or Firm* — Christensen O'Connor Johnson Kindness PLLC

(57) ABSTRACT

Disclosed herein are fluff pulp compositions, absorbent articles comprising the fluff pulp compositions, and related methods. The fluff pulp compositions comprise a chemiluminescent system configured to produce visible light upon contact with an aqueous system. Representative absorbent articles include disposable diapers and adult incontinence products. Representative chemiluminescent systems include bioluminescent systems.

46 Claims, 9 Drawing Sheets

Coelenterazine (native coelenterazine)

Coelenterazine 400a

(51) Int. Cl.
  *A61L 15/28* (2006.01)
  *A61L 15/40* (2006.01)
  *A61L 15/56* (2006.01)
  *A61F 13/84* (2006.01)
  *A61F 13/511* (2006.01)
  *A61F 13/513* (2006.01)
  *A61F 13/49* (2006.01)
  *A61F 13/51* (2006.01)
  *A61F 13/42* (2006.01)

(52) U.S. Cl.
  CPC ..... *A61F 13/51305* (2013.01); *A61F 13/8405* (2013.01); *A61F 2013/426* (2013.01); *A61F 2013/427* (2013.01); *A61F 2013/428* (2013.01); *A61F 2013/429* (2013.01); *A61L 2300/30* (2013.01); *A61L 2300/442* (2013.01)

(56) References Cited

U.S. PATENT DOCUMENTS

| | | |
|---|---|---|
| 3,702,610 A | 11/1972 | Sheppard |
| 3,731,685 A | 5/1973 | Eidus |
| 3,759,261 A | 9/1973 | Wang |
| 3,918,454 A | 11/1975 | Korodi |
| 3,952,746 A | 4/1976 | Summers |
| 4,022,211 A | 5/1977 | Timmons |
| 4,192,311 A | 3/1980 | Felfoldi |
| 4,231,370 A | 11/1980 | Mroz |
| 4,705,513 A | 11/1987 | Sheldon |
| 4,738,674 A | 4/1988 | Todd |
| 4,931,051 A | 6/1990 | Castello |
| 5,447,689 A * | 9/1995 | Gibboni ............... G01N 33/525 422/408 |
| 5,947,943 A | 9/1999 | Lee |
| 6,060,261 A | 5/2000 | Ryufuku et al. |
| 6,066,774 A * | 5/2000 | Roe .................. A61F 13/42 604/358 |
| 6,113,886 A | 9/2000 | Bryan |
| 6,152,358 A | 11/2000 | Bryan |
| 6,416,960 B1 | 7/2002 | Bryan |
| 6,521,304 B1 | 2/2003 | Kajiyama et al. |
| 2004/0172000 A1 | 9/2004 | Roe et al. |
| 2004/0209255 A1* | 10/2004 | Koster ................ C12Q 1/6834 435/6.14 |
| 2005/0133387 A1 | 6/2005 | Cohen et al. |
| 2006/0053505 A1 | 3/2006 | Bryan |
| 2007/0026209 A1 | 2/2007 | MacDonald |
| 2010/0004613 A1 | 1/2010 | Cohen |
| 2011/0224638 A1 | 9/2011 | Cohen |
| 2013/0088853 A1 | 4/2013 | Kingsley et al. |
| 2014/0045761 A1 | 2/2014 | Gibson |

FOREIGN PATENT DOCUMENTS

| | | |
|---|---|---|
| EP | 1 393 702 A1 | 3/2004 |
| WO | 00/65083 A2 | 11/2000 |
| WO | 2010/003038 A2 | 1/2010 |

OTHER PUBLICATIONS

International Search Report dated Dec. 28, 2015, issued in corresponding International Application No. PCT/US2015/053400, filed Oct. 1, 2015, 2 pages.

Extended European Search Report dated Jun. 4, 2018, issued in corresponding European Application No. 15851372.1, filed Oct. 1, 2015, 8 pages.

* cited by examiner

Coelenterazine (native coelenterazine)

Coelenterazine 400a

Coelenterazine cp

Coelenterazine f

Coelenterazine fcp

Coelenterazine e

Coelenterazine h

Coelenterazine n

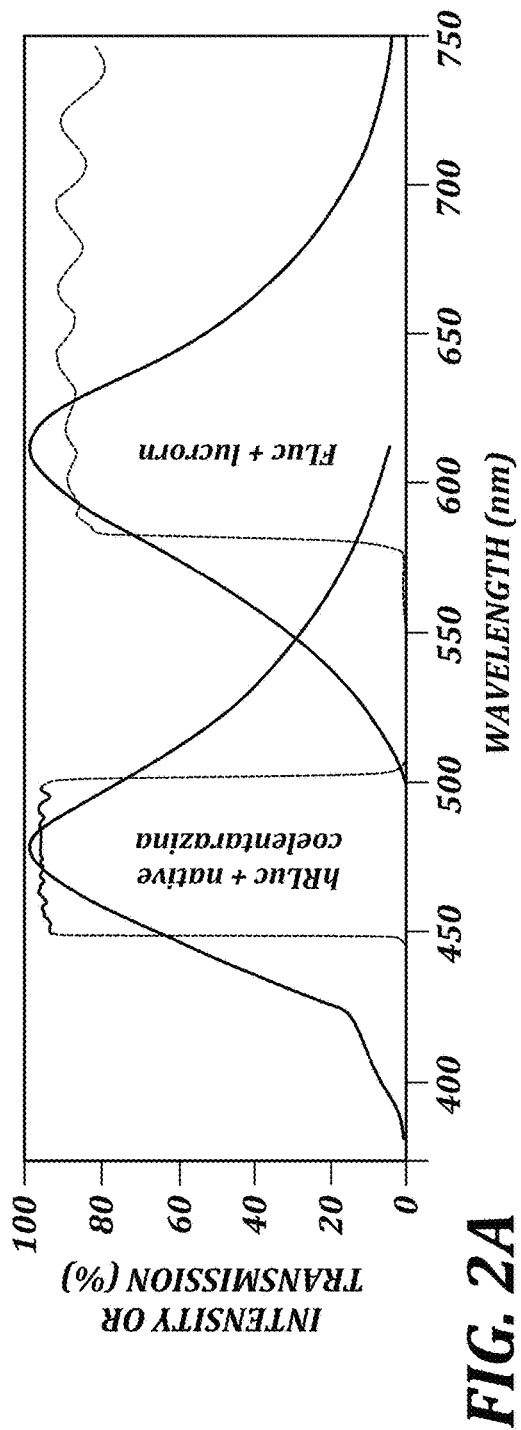
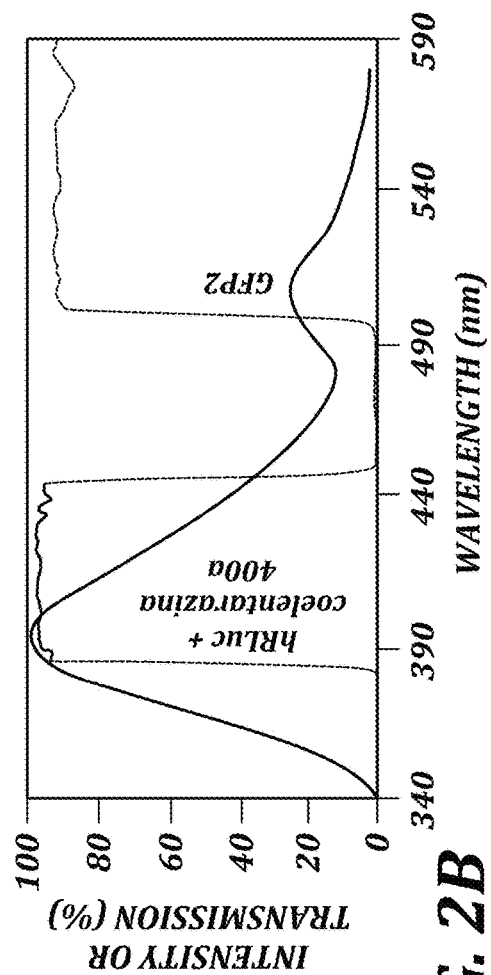
FIG. 2A
FIG. 2B

CHEMILUMINESCENT WETNESS INDICATOR FOR ABSORBENT PRODUCTS

TECHNICAL FIELD

This disclosure relates to treated fluff pulp compositions, and in particular to fluff pulp compositions and absorbent articles incorporating fluff pulp compositions, which integrate a chemiluminescent system configured to produce visible light upon contact with an aqueous system such as a fluid insult.

BACKGROUND

Personal care absorbent products, such as infant diapers, adult incontinent pads, and feminine care products, typically contain a fluid absorbent core. Many absorbent articles include the fluid absorbent core disposed between a top sheet and a back sheet. The top sheet is typically formed from a fluid-permeable material adapted to promote fluid transfer into the absorbent core, such as upon a liquid insult, usually with minimal fluid retention by the top sheet. U.S. southern pine fluff pulp is commonly used in the absorbent core, generally in the form of a fibrous matrix, and sometimes in conjunction with a superabsorbent polymer (SAP) dispersed throughout the fibrous matrix. This fluff pulp is recognized worldwide as the preferred fiber for absorbent products, based on factors such as the fluff pulp's high fiber length, fiber coarseness, and its relative ease of processing from a wet-laid and dried pulp sheet to an air-laid web. The raw material for this type of cellulosic fluff pulp is Southern Pine (e.g., Loblolly Pine, *Pinus taeda* L.,). The raw material is renewable, and the pulp is easily biodegradable. Compared to SAP, these fibers are inexpensive on a per mass basis but tend to be more expensive on per unit of liquid held basis. These fluff pulp fibers mostly absorb within the interstices between fibers. For this reason, a fibrous matrix readily releases acquired liquid on application of pressure. The tendency to release acquired liquid can result in significant skin wetness during use of an absorbent product that includes a core formed exclusively from cellulosic fibers. Such products also tend to leak the acquired liquid because liquid is not effectively retained in such a fibrous absorbent core.

SAPs are water-swellable, generally water-insoluble absorbent materials having a high absorbent capacity for fluids. They are used in absorbent articles like baby diapers or adult incontinent products to absorb and hold body fluids. SAP, upon absorption of fluids, swells and becomes a gel holding more than its weight of such fluids. The SAPs in common use are mostly derived from acrylic acid. Acrylic acid based polymers also comprise a meaningful portion of the cost structure of diapers and incontinent pads. SAPs are designed to have high gel strength (as demonstrated by high absorbency under load or AUL). The high gel strength (upon swelling) of currently used SAP particles helps them to retain significant void space between particles, which is helpful for rapid fluid uptake. However, this high "void volume" simultaneously results in significant interstitial (between particles) liquid in the product in the saturated state. When there is interstitial liquid the "rewet" value or "wet feeling" of an absorbent product is compromised.

Some absorbent articles, such as diapers or adult incontinence pads, also include an acquisition and distribution layer (ADL) for the collection and uniform and timely distribution of fluid from a fluid insult to the absorbent core. An ADL is usually placed between the top sheet and the absorbent core, and normally takes the form of composite fabric with most likely the top-one third of the fabric having low density (higher denier fiber) with relatively large voids and higher void volume for the effective acquisition of the presented fluid, even at relatively higher discharge rates. The middle one-third of the composite fabric of the ADL is usually made of higher density (low denier) fibers with smaller voids, while the lower one-third of the fabric is made of even higher density (lower and smaller denier) fibers and yet with finer voids. The higher density portions of the composite have more and finer capillaries and hence develop greater capillary pressure, thus moving greater volumes of fluid to the outer regions of the structure thus enabling the proper channelization and distribution of the fluid in an evenly fashion to allow the absorbent core to take up all of the liquid insult in a time bound manner to allow SAP within the absorbent core to hold and to gel the insult neither too slow nor too fast. The ADL provides for more rapid liquid acquisition (minimizing flooding in the target zone), and ensures more rapid transport and thorough distribution of the fluid into the absorbent core.

As noted above, the absorbent core is adapted to retain fluid, and as such may consist of one or more layers, such as layers to acquire, distribute, and/or store fluid. In many cases, a matrix of cellulose fibers, such as in the form of an air-laid pad and/or non-woven web, is used in (or as) the absorbent core of absorbent articles. In some cases, the different layers may consist of one or more different types of cellulose fibers, such as cross-linked cellulose fibers. The absorbent core may also include one or more fluid retention agents, such as one or more SAPs, distributed throughout the fiber matrix, usually as particles.

The back sheet is typically formed from a fluid-impermeable material to form a barrier to prevent retained fluid from escaping.

Whatever the structure, when the absorbent article is wet from one or more liquid insults, the chances for the fluid coming in contact with the skin increases profoundly, and if left unchanged for a long time can result in diaper rash for infants or dermatitis problem in adults, thereby posing a skin wellness hazard. However, in general, the only way to know whether the diaper or the incontinent pad is dry or wet is to physically inspect it. During day time this may not pose a significant problem because a caregiver can check the diapers or adult incontinent products as many times as desired. However, inspections during night time can be a discomfort to the baby as well as to the adult, disturbing their sleep. Moreover, frequent night time inspections, such as several times in a single night, can disrupt the wearer's sleeping pattern, which poses health hazard to baby as well as the adult patient.

In addition, it is typical that an article of clothing, such as pants, pajamas, and/or undergarments, is worn over the diaper or absorbent article. Accordingly, even absorbent articles that incorporate different types of wetness and/or moisture indicators pose difficulties in timely discovery of an insult.

As a result, there it typically a time lapse between the insult and its discovery. If this time period is prolonged then there exists the possibility of developing diaper rash, skin irritation, and/or skin flaking. These conditions can be very painful for those affected. This is particularly true for babies and those adults in care-giving facilities, and particularly true for night time insults, which can lead to longer periods prior to changing the absorbent article.

Previous moisture indicators incorporated into absorbent articles use color change as a visual indication of wetness detection. Inks that appear, or disappear, based on contact with liquid are popular mechanisms for wetness detection. Fluorescence has also been used for wetness detection, such as by incorporating a compound that fluoresces in the presence of a liquid. The mechanisms for such indicators generally fall into three broad categories: (1) imprinting a moisture indicating pattern on one of the piles of the absorbent article; (2) discrete moisture-indicating strips or layers that are incorporated between the layers of the absorbent article; and (3) a discrete (i.e., not part of the absorbent article's construction) indicating strip that is fastened to the interior of the absorbent article immediately prior to use.

Whatever the mechanism, these visual indicators are all deficient in low-light (e.g., night time) situations. Appearing or disappearing inks must be directly visually detected, such that the caregiver can see the absorbent product. In low-light situations, this may require both a light source (e.g., overhead light or flashlight), as well as the removal of covering garments (e.g., pajamas or undergarments). Fluorescent indicators suffer similar issues, in that they require an external light source to excite the fluorescent compound. Such excitation is typically provided by exposing the indicator to UV light (which presents health concerns to the wearer and caregiver) and must be in direct optical communication with the fluorescent compound, which then requires removal of covering garments, blankets, etc. Therefore, the use of visual indicators previously used to detect wetness in absorbent garments suffers many disadvantages in low-light situations, which greatly reduces the usefulness of their indication mechanisms.

Each of these solutions to wetness detection for absorbent articles is deficient for the needs of night insult detection. Chiefly, all technologies do not reliably trigger, and even when they do, require direct, lighted visual inspection to detect.

Therefore, present absorbent articles are inadequate when alerting a caregiver to insults occurring at night and/or under garments.

SUMMARY

In one aspect, a fluff pulp composition is provided. In one embodiment, the fluff pulp composition includes fluff pulp and a chemiluminescent system that is configured to produce visible light upon contact with an aqueous system. Representative chemiluminescent systems include bioluminescent systems, such as the reaction between a luciferin and a luciferase. Methods of manufacturing the fluff pulp composition are also provided.

In another aspect, an absorbent article is provided and methods of manufacturing the absorbent article. In one embodiment, the absorbent article includes a top sheet that is liquid permeable, a back sheet that is liquid impermeable, fluff pulp disposed between the top sheet and the back sheet, and a chemiluminescent system configured to produce visible light upon contact with an aqueous system.

Representative absorbent articles include disposable diapers and adult incontinence products.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 2A and 2B graphically illustrate spectral properties of chemiluminescent systems in accordance with embodiments disclosed herein;

DETAILED DESCRIPTION

Disclosed herein are fluff pulp compositions, absorbent articles, and related methods. The fluff pulp compositions and absorbent articles comprise a chemiluminescent system configured to produce visible light upon contact with an aqueous system. Representative absorbent articles include disposable diapers and adult incontinence products. Representative chemiluminescent systems include bioluminescent systems. In certain embodiments, the absorbent articles incorporate the fluff pulp compositions.

Chemiluminescence results from a chemical reaction that produces light and therefore provides a lighted indication of moisture that can be seen in low light and/or in the absence of light, and through clothes. Furthermore, chemiluminescence requires no external excitation light, as is required for photoluminescent (e.g., fluorescence) indicators. Accordingly, by generating visible light upon contact with an aqueous system (e.g., urine), the disclosed embodiments greatly enhance the ability of absorbent articles to indicate the occurrence of an insult in darkened conditions (e.g., at night). Moreover, by generating light that can be seen through clothing, a caregiver may be able to ascertain the occurrence of an insult without having to move or disturb the infant or adult wearer of such an absorbent article, such as during sleep. Therefore, the compositions and articles provided herein may provide the distinct advantages of insult indication at night and through clothes, which may reduce or even eliminate the need for caregivers to disturb the sleep (e.g., by pulling down clothes and/or shining a light) of one wearing an absorbent article in order to test for an insult. Further, because visible light is produced by the chemiluminescent systems disclosed herein, there is no need to expose the absorbent article and/or the wearer to UV light in order to determine whether an insult has occurred, allowing health concerns associated with UV radiation to be avoided.

Figure 5:
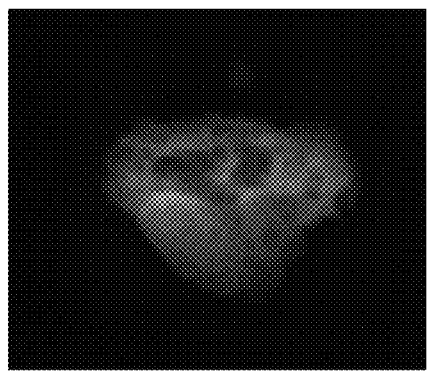
FIGS. 5-8 photographically depict example absorbent articles in accordance with embodiments disclosed herein.

The low-light detection of embodiments of the disclosed fluff pulp compositions and absorbent articles is illustrated in FIG. 5, which is a photograph of an absorbent article (diaper) with the chemiluminescent fluff pulp composition incorporated. In FIG. 5, a mock insult (saline solution) was applied and the image was captured showing chemiluminescence shining through the diaper back sheet and lightweight cotton fabric for easy visual detection in low-light conditions. FIG. 5 is contrasted with comparative FIG. 9B, which is a similar absorbent article formed using fluorescent instead of chemiluminescent fluff pulp. The comparative absorbent article does not function through the diaper material, due to blocked excitation via an external light source.

Therefore, activation of the fluorescent wetness indicator requires removal of clothing, etc. and application of an excitation light (e.g., UV light) in order to visually detect an insult. Chemiluminescence requires neither removal of clothing or excitation light.

The improved ease with which an insult can be detected allows the caregiver to check for an insult more frequently, due to the reduced interruption required. More frequent checks may allow an insult to be detected sooner and the absorbent article changed soon after the insult, thereby reducing the amount of time the insult contacts the wearer's skin, as well as reducing the possibility of fluid from multiple insults contacting the wearer's skin. The skin health and general comfort of the wearer are improved when the length of time that fluid is in contact with the skin is reduced.

In one aspect, a fluff pulp composition is provided. In one embodiment, the fluff pulp composition includes fluff pulp and a chemiluminescent system that is configured to produce visible light upon contact with an aqueous system.

Chemiluminescent System

The chemiluminescent system is configured to produce visible light upon contact with an aqueous system. The aqueous system initiates the chemiluminescence reaction in order to produce light. As used herein, the term "aqueous system" refers to water or water-containing compositions. In the context of this disclosure, such water-containing compositions are generally in the form of body fluid, such as urine, menses, fecal matter, and so forth. The occurrence of the release of bodily fluid (or the fluid itself) is referred to herein as an "insult," or "liquid insult" or "fluid insult." Accordingly, the chemiluminescent systems of the present disclosure produce visible light upon insult of an absorbent article in which the system is incorporated.

In being configured to produce visible light upon contact with an aqueous system, the chemiluminescent system includes at least one compound or material that luminesces when contacted with an aqueous system. In one embodiment water is the component of the aqueous system that initiates the chemiluminescence.

In one embodiment, the chemiluminescent system includes two or more materials that luminesce when contacted with an aqueous system. In this embodiment, there are two or more materials that together do not luminesce without the presence of the aqueous system.

Representative chemiluminescent systems that include two or more materials include bioluminescent systems, such as a system that includes a luciferin and a luciferase.

Bioluminescence is light that is produced by a chemical reaction that occurs within the body or in the secretions of certain type of organisms. Bioluminescence involves the combination of two types of substances in a light-producing reaction. Bioluminescence requires at least two different chemicals: a luciferin and a luciferase. Luciferin is the compound that actually produces the light. Luciferase is an enzyme that catalyzes the reaction. In some cases luciferin is a protein known as a photoprotein, and the light making process requires a charged ion (e.g., a cation such as calcium) to activate the reaction. Photoprotein is a variant of luciferase in which factors required for light emission (including luciferin and oxygen) are bound together as one unit. Often, the bioluminescence process requires the presence of a substance such as oxygen or adenosine triphosphate (ATP) to initiate the oxidation reaction. The reaction rate for the luciferin is controlled by the luciferase or photoprotein. The luciferin-luciferase reaction can also create byproducts such as inactive oxyluciferin and water.

Luciferin and luciferase are generic names rather than specific materials. For example, the luciferin coelenterazine (natural form) is common in marine bioluminescence but variants can be chemically synthesized and these various forms are collectively called luciferins. In another example, dinoflagellates (marine planktons) that obtain food through photosynthesis use a luciferin that resembles the chlorophyll structure.

The mechanism of light production through a chemical reaction differentiates bioluminescence from other optical phenomenon such as fluorescence or phosphorescence.

For example, fluorescent molecules do not emit their own light. They need an external photon source to excite the electrons to a higher energy state. On relaxation from the high energy state to their natural ground state, they release their acquired energy as a light source, but usually at a longer wavelength. Since the excitation and relaxation occurs simultaneously, fluorescent light is seen only when illuminated (excited).

The term phosphorescence technically refers to a special case of optically excited light emission where the relaxation from the excited state to ground state, unlike the fluorescence, is not immediate, and the photon emission persists for seconds to minutes after the original excitation.

The technical distinction between bioluminescence and fluorescence is sometimes blurred in a practical context but technically they are two distinct phenomena. In most cases, a bioluminescent can be an autofluorescent but the reverse is not true for a fluorescent; the latter still requires photon for excitation to emit light. In some cases a bioluminescent cnidarians or crustaceans or fish can contain a fluorescent protein like Green Fluorescent Protein (GFP) and the light emitted from the bioluminescent would act as photons to excite the GFP. The GFP in turn under relaxed state would emit a light of different wave length (most probably of higher wave length) than the wavelength of the bioluminescent light that it has received as photon. In this example, the GFP may be excited by a blue light emitted by the bioluminescent (wave length 470 nm) but in turn would emit a green light under its relaxed state (wave length of 510 nm to 520 nm).

Bioluminescent systems can be incorporated into the fluff pulp compositions or absorbent articles in any manner that produces the desired chemiluminescence.

In one embodiment, the fluff pulp composition or absorbent product comprises a luciferin selected from the group consisting of coelenterazine, dinoflagellate luciferin, bacterial luciferin, fungal luciferin, firefly luciferin, and vargulin. With regard to coelenterazine, there are many variants, any of which can be used in the fluff pulp composition. Certain embodiments of coelenterazine consistent with this disclosure comprise one or more of native coelenterazine, methyl coelenterazine, coelenterazine 400a (2-2'(4-dehydroxy)) coelenterazine, coelenterazine e, coelenterazine f, coelenterazine h, coelenterazine i, coelenterazine n, coelenterazine cp, coelenterazine ip, coelenterazine fcp, and coelenterazine hcp. As a further example, the coelenterazine may be one or more of native coelenterazine, coelenterazine 400a, methyl coelenterazine, coelenterazine f, coelenterazine cp, coelenterazine fcp, and coelenterazine hcp. As yet a further example, the coelenterazine may be one or more of coelenterazine 400a, methyl coelenterazine and coelenterazine fcp. As yet a further example, the coelenterazine may be one or more of coelenterazine 400a, methyl coelenterazine, and coelenterazine hcp. In yet another example, the coelenterazine may be may be one or more of coelenterazine 400a and coelenterazine hcp.

In one embodiment, the luciferin has a concentration of 0.01% to 2%, by weight of the fluff pulp. In one embodiment, the luciferin has a concentration of 0.05% to 1.5%, by weight of the fluff pulp. In one embodiment, the luciferin has a concentration of 0.1% to 1%, by weight of the fluff pulp.

In one embodiment, the fluff pulp composition or absorbent product comprises luciferase selected from the group consisting of *Gaussia* luciferase (GLuc), *Renilla* luciferase (RLuc), dinoflagellate luciferase, firefly luciferase, fungal luciferase, bacterial luciferase, and vargula luciferase. Certain embodiments of the luciferase consistent with this disclosure comprise one or more of *Gaussia* luciferase, *Renilla* luciferase, dinoflagellate luciferase, and firefly luciferase. As a further example, the luciferase may be one or more of *Gaussia* luciferase, *Renilla* luciferase, dinoflagellate luciferase, and firefly luciferase. In yet a further example, the luciferase may be one or more of *Gaussia* luciferase and *Renilla* luciferase.

In one embodiment, the luciferase has a concentration of 0.1% to 20%, by weight of the fluff pulp. In one embodiment, the luciferase has a concentration of 0.5% to 15%, by weight of the fluff pulp. In one embodiment, the luciferase has a concentration of 1% to 10%, by weight of the fluff pulp.

In one embodiment, the chemiluminescent system comprises coelenterazine as the luciferin and *Gaussia* or *Renilla* luciferase.

Representative luciferins include those of the coelenterazine family. Coelenterazine in its native form as well as its analogs have different luminescent characteristics due variation in their structural moieties. Given structural variations within the coelenterazine family, some are good substrates for luciferase, whereas some are not. Below is a brief description of native coelenterazine and representative analogs.

Figure 1A:
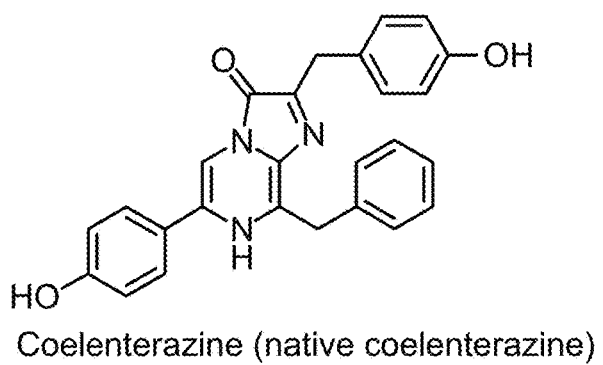
FIGS. 1A-1H are chemical structures of representative luciferin compounds useful in chemiluminescent systems in accordance with embodiments disclosed herein.

Coelenterazine (native form), illustrated in FIG. 1A, is a luminescent enzyme substrate for *Renilla* luciferase. *Renilla* luciferase/coelenterazine has also been used as the bioluminescence donor in bioluminescence resonance transfer (BRET) studies.

Figure 1B:
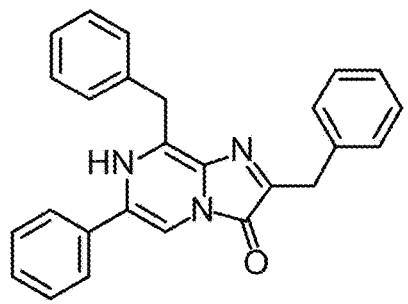

Coelenterazine 400a, illustrated in FIG. 1B, is a derivative of coelenterazine and is a good substrate for *Renilla* (*reniformis*) luciferase (RLuc), but does not oxidize well with *Gaussia* luciferase (GLuc). It is the preferred substrate for BRET (bioluminescence resonance energy transfer) because its emission maximum of 400 nm has minimal interference with the GFP emission.

Fluorescence resonance energy transfer (FRET), BRET, resonance energy transfer (RET), and electronic energy transfer (EET) are mechanisms describing energy transfer between two light-sensitive molecules (chromophores) and usually define the interference of a luminescencent chemical with another luminescencent chemical's energy transfer, thus decreasing the energy state the latter can be taken to which is critical in terms of relaxation energy released back to the ground state. A donor chromophore, initially in its electronic excited state, may transfer energy to an acceptor chromophore through nonradiative dipole-dipole coupling. The efficiency of this energy transfer is inversely proportional to the sixth power of the distance between donor and acceptor, making FRET extremely sensitive to small changes in distance. Measurements of FRET efficiency can be used to determine if two fluorophores are within a certain distance of each other. Such measurements are used as a research tool in fields including biology and chemistry.

For example, BRET in the presence of *reniformis* Luciferase (RLuc) by coelenterazine 400a is compared to coelenterazine (native form) and clearly shows minimal interference with the GFP emission, as illustrated in FIGS. 2A and 2B, wherein "hRluc" is *Renilla* luciferase and a coelenterazine h bioluminescence system; "FLuc" is *Renilla* luciferase with a native coelenterazine system; "lucroron" is a luciferase and luciferin system with GFP2 as a photon acceptor that fluoresces resulting from emission from the hRLuc bioluminescence; and "GFP2" is Green Fluorescent Protein (2nd generation).

Figure 1C:
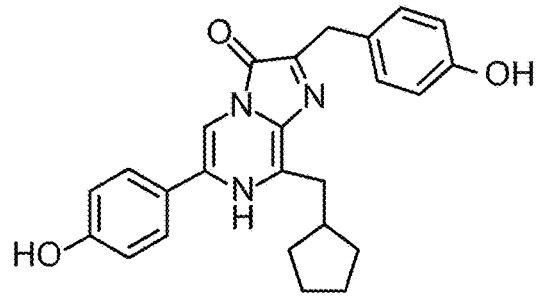

Coelenterazine cp, illustrated in FIG. 1C, in a coelenterazine-aeoquorin complex generates luminescence intensity 15 times higher than coelenterazine (native form).

Figure 1D:
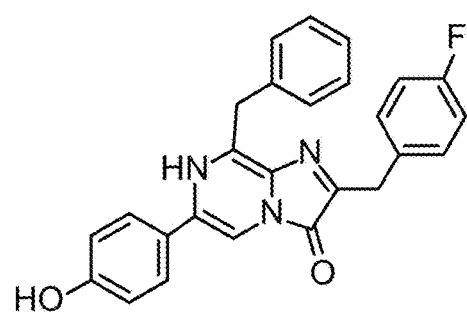

Coelenterazine f, illustrated in FIG. 1D, has 20 times higher luminescence intensity (coelenterazine-apoaequorin complex) than the native form coelenterazine, while its emission maximum is about 8 nm longer than that of the native form.

Figure 1E:
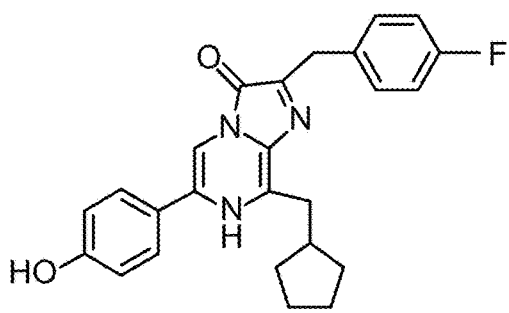

Coelenterazine fcp, illustrated in FIG. 1E, is an analog wherein the o-benzene structure in the elenterazine moiety of coelenterazine f structure is replaced with a cyclic pentane (similar to coelenterazine cp). Coelenterazine fcp has luminescence intensity 135 times greater than that of coelenterazine (native form).

Coelenterazine fcp complexes with aequorin to form a coelenterazine fcp-apoaequorin complex and as a substrate for aequorin has a relative luminescence intensity of 135 times as compared to native form coelenterazine. However, coelenterazine fcp is a poor substrate for *Renilla* Luciferase.

Figure 1F:
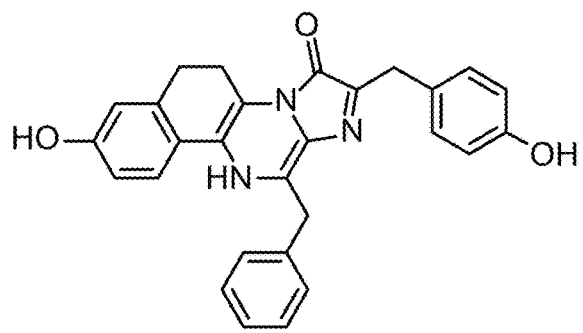
Figure 1G:
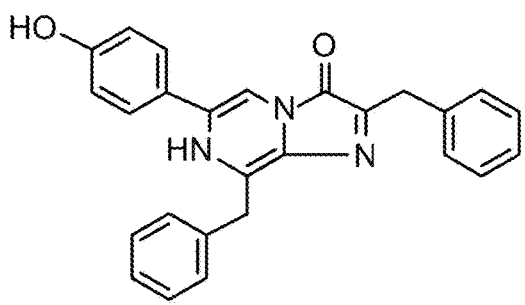
Figure 1H:
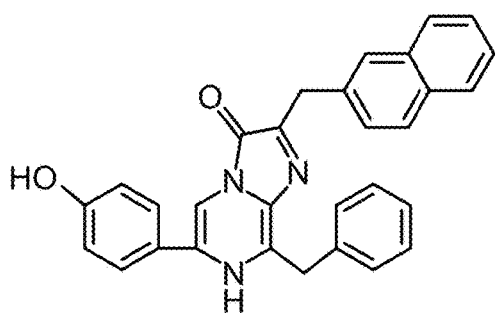

Other representative analogs of coelenterazine, as a substrate for *Renilla* Luciferase enzyme, are coelenterazine e, h and n, illustrated in FIGS. 1F, 1G, and 1H, respectively. While these three analogs are good to excellent substrates for *Renilla* Luciferase, they are poor substrates for apoaequorin.

The luminescent properties of coelenterazine analogs vary. For example, certain analogs emit less light (as measured as lumens) but with higher luminescent intensity (lumens/steradian). Table 1 lists the luminescent properties of coelenterazine (native form) and its analogs with *Renilla* Luciferase. Luminescent intensity is reported as a % initial intensity. For example, an analog having an initial intensity of 900% is 20 times intense as compared to the native coelenterazine with an initial intensity of 45%.

TABLE 1

Luminescent Properties of Selected Coelenterazine Analogs with *Renilla* Luciferase

| Analog | $\lambda_{em}$(nm) | Total Light (%) | Initial Intensity (%) |
|---|---|---|---|
| native | 475 | 100 | 45 |
| cp | 470 | 23 | 135 |
| e | 418, 475 | 137 | 900 |
| f | 473 | 28 | 45 |
| h | 475 | 41 | 135 |
| n | 475 | 47 | 900 |

Figure 3:
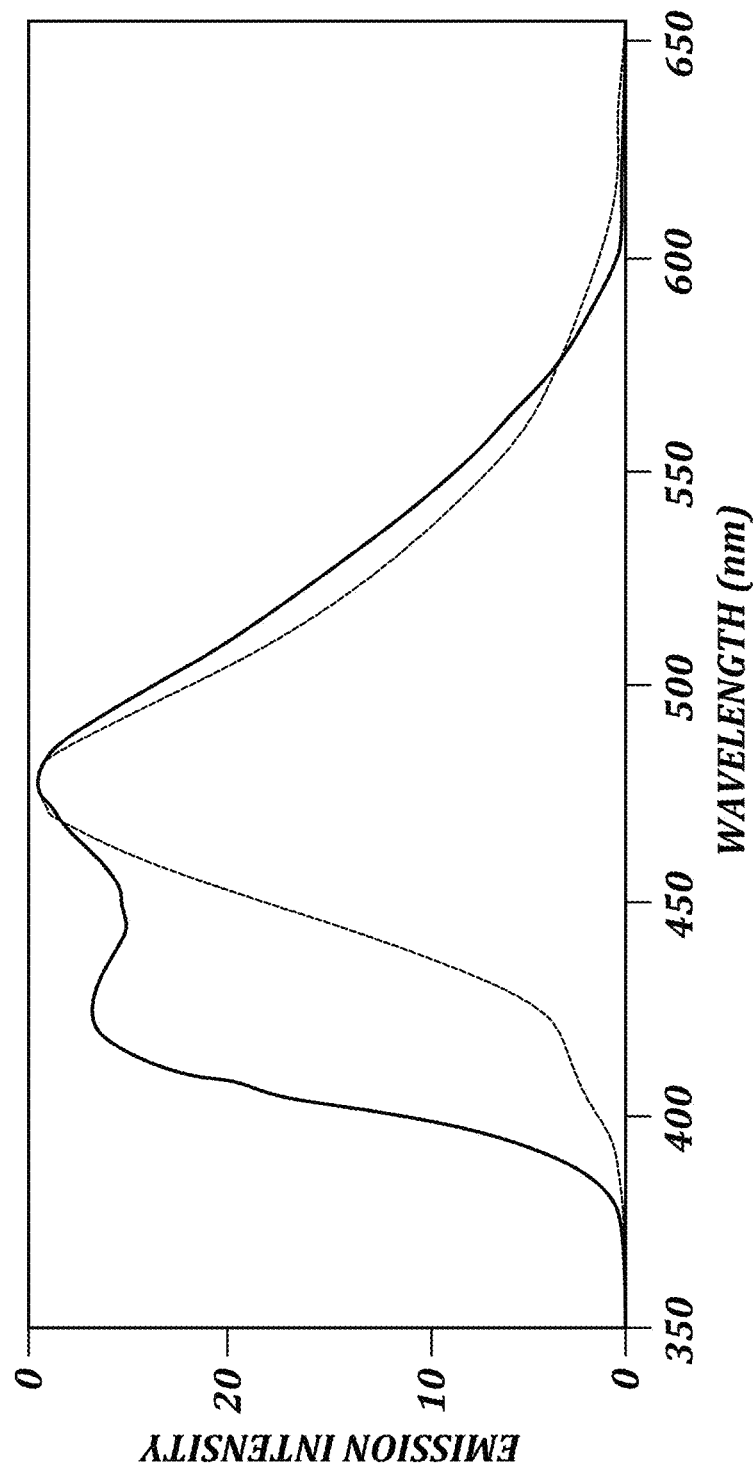
FIG. 3 graphically illustrates spectral properties of representative luciferins in accordance with embodiments disclosed herein.

The emission spectra (normalized) of coelenterazine e (with a luminescent intensity 20 times higher than that of native coelenterazine) and native coelenterazine are illustrated in FIG. 3. In FIG. 3, coelenterazine e (solid line) and native coelenterazine (dotted line) are measured in the presence of recombinant *Renilla* luciferase (RLuc). Note there are two intensity peaks for coelenterazine e, one at a wavelength ($\lambda_{em}$) of 418 nm and the other at 475.

Visible light is produced by the chemiluminescent system. The visible light is visually detectable by a caregiver in the dark and through clothing, and as such the visible light has a wavelength, intensity, and duration sufficient to provide the necessary indication. These spectral characteristics of the chemiluminescent system can be tailored based on the chemiluminescent compound or compounds. For example, in bioluminescent systems, the luciferin and luciferase can be selected to produce the desired light characteristics. Depending on the bioluminescent system used, different spectral characteristics can occur. In the presence of superoxide anions and/or peroxynitrile compounds, coelenterazine can also emit light independent of enzyme (luciferase) oxidation, a process known as autoluminescence.

The chemiluminescent system can be tailored to produce particular colors of visible light. As noted above in Table 1, even within the coelenterazine family, the emission wavelength can range from about 400 nm (violet) to about 475 nm (blue with green tint).

With regard to duration, the duration of the light emitted may be controlled by the selection of the coelenterazine (luciferin), in native form versus its analogues, and the enzyme (Luciferase), for example *Gaussia* versus *Renilla*. The ratio and the concentration of luciferin and luciferase used may also modify the duration of light emission. To give an illustrative and non-limiting example, the luciferin analogue, coelenterazine e, has a total light of 130% and initial intensity of 900% (see FIG. 3) over native coelenterazine. By judiciously selecting the concentration of coelenterazine e and *Renilla* luciferase, the duration of the visible light emitted can last as much as 8 to 10 hours.

In one embodiment, the visible light has a duration of 0.5 to 6 hours. In another embodiment, the visible light has a duration of 1 to 4 hours. In another embodiment, the visible light has a duration of 2 to 3 hours.

With regard to intensity, quantum efficiency of the chemiluminescence contributes to the intensity, depth, and hue of the color of the emission.

Quantum efficiency (QE) is the fraction of photon flux used to excite a luminescence chemical to elevate it to higher energy state. Quantum efficiency is one of the most important parameters used to evaluate the quality of a detector and is often called the "spectral response" to reflect its wavelength dependence. It is defined as the number of signal electrons created per incident photon. In some cases it can exceed 100% (i.e. when more than one electron is created per incident photon). If the spectral response exceeds 100%, then the intensity and depth of the color emitted is vivid, but depending on the status of the excited state of the primary electron, the duration of the emission will be determined (i.e., the higher the excited state, the more time it takes to return to the ground (normal) state).

Spectral responsivity is a similar measurement, but it has different units; the metric being the amperes or watts (i.e., how much current comes out of the device per incoming photon of a given energy and wavelength).

Both the quantum efficiency and the spectral responsivity are functions of the photons' wavelength. For example, in the case of the luciferin coelenterazine, between the native form and one of its analogs, coelenterazine e, the latter has not only high light intensity but emits 30% more light energy than the former, because the latter upon excitation by a given quanta (hv) of incident photon generates two electrons and the primary electron at wavelength 475 has the same emission intensity as native coelenterazine but with lumen intensity 20 times greater than that of the native product. Accordingly, the light emitted by the excited coelenterazine analog would be twenty times brighter than the native form but with a total light energy of 130% will last longer than the native form.

The wavelength determines the color of the emitted visible light.

In one embodiment, the fluff pulp composition includes a luciferin and a luciferase. Such a fluff pulp has both elements of the chemiluminescent system required to luminesce upon contact with an aqueous system. However, in another embodiment, the fluff pulp composition includes at least one component selected from a luciferin and a luciferase. In such an embodiment, the fluff pulp composition may include only one of a luciferin and a luciferase. Such a fluff pulp composition may be incorporated into an absorbent article such that the other one of the luciferin and the luciferase may be disposed in a top sheet or other layer of the absorbent article, such that the two components are combined only when carried by a liquid insult (e.g., water from an aqueous system passing through the top sheet into the fluff pulp composition). In one embodiment the fluff pulp composition comprises a luciferin but not a luciferase. In one embodiment the fluff pulp composition comprises a luciferase but not a luciferin.

Photoluminescent Compound

In one embodiment, the chemiluminescent system includes a photoluminescent (e.g., fluorescent and/or phosphorescent) compound having a photoluminescent absorption wavelength range that overlaps with a chemiluminescent emission wavelength range of the chemiluminescent system, wherein the photoluminescent compound has a photoluminescent emission wavelength range that is different from the chemiluminescent emission wavelength range. The photoluminescent compound can be used to "shift" the emission wavelength of the chemiluminescent system. For example, photoluminescence can be used to change or otherwise tailor the color (or other spectral quality) of the visible light.

While the chemiluminescent system produces visible light, the chemiluminescence itself need not necessarily be in the visible spectrum. The chemiluminescence produces electromagnetic radiation in some wavelength range, but the disclosed embodiments are not limited to chemiluminescent emission in the visible range. Accordingly, in certain embodiments the chemiluminescent system may produce chemiluminescent emission that is not in the visible wavelength range. In such embodiments, a photoluminescent compound may be used to shift the emission spectrum into the visible range.

In one embodiment, the photoluminescent compound is selected from the group consisting of a fluorescent compound and a phosphorescent compound. Fluorescent compounds can include, but are not confined to, xanthene derivatives such as fluorescein, rhodamine, Oregon green, eosin and Texas red; cyanine derivatives such as indocatbocyanine; napthene derivatives; coumarin derivatives; oxadiazole derivatives such as pyridyloxazole; anthracene derivatives such as anthraquinone; pyrene derivatives such as Cascade blue; acridine derivatives such as proflavin, acridine orange, and acridine yellow; arylmethine derivatives such as auramine, crystal violet, and malachite green; tetrapyrrole derivatives such as porphin; bilirubin; phosphorescent compounds such as silver activated zinc sulfide and doped strontium aluminate; and so forth.

In one embodiment, the photoluminescent compound is present in an amount of 0.01% to 2.0% by weight of the fluff pulp. In one embodiment, the photoluminescent compound is present in an amount of 0.05% to 1.5% by weight of the fluff pulp. In one embodiment, the photoluminescent compound is present in an amount of 0.1% to 1.0% by weight of the fluff pulp.

The photoluminescent compound can be disposed in the fluff pulp or, if incorporated into an absorbent article, in an adjacent layer (e.g., top sheet). Of importance is that the photoluminescent compound is in optical communication (at emission and excitation wavelengths) with the chemiluminescence. Therefore, the photoluminescent compound can even be disposed on a back sheet of an absorbent article.

pH Buffer

In one embodiment a pH buffer is added to the fluff pulp composition. The pH buffer can be configured to modify the spectral properties such as intensity of the chemiluminescent system. For example, pH control can be used to improve the efficiency of the chemiluminescence. Exemplary improvements to the efficiency of the chemiluminescence include extending or otherwise modifying the duration of emission so as to provide a caregiver a desired amount of time to detect an insult. Accordingly, in one embodiment the pH buffer is configured to increase the efficiency of the visible light from the chemiluminescent system upon contact with the aqueous system.

In one embodiment, the pH buffer is selected from the group consisting of sodium bicarbonate, sodium acetate, sodium citrate, sodium lactate, sodium lactate citrate, sodium borate, calcium acetate, calcium citrate, calcium bromide, calcium gluconate, calcium lactate, calcium lactate malate, calcium carbonate, calcium bicarbonate, and potassium dihydrogen phosphate. Calcium salts are particularly effective in increasing the efficiency of the chemiluminescence reaction.

In one embodiment, the fluff pulp composition comprises a pH buffer configured to provide buffering of the aqueous system between a pH of 4.0 to 8.5. In one embodiment, the fluff pulp composition comprises a pH buffer configured to provide buffering of the aqueous system between a pH of 5.0 to 7.5. In one embodiment, the fluff pulp composition comprises a pH buffer configured to provide buffering of the aqueous system between a pH of 5.5 to 6.5.

The pH buffer can be disposed in the fluff pulp or, if incorporated into an absorbent article, in an adjacent layer (e.g., top sheet). Of importance is that the pH buffer contacts the chemiluminescent system upon insult. Therefore, if the pH buffer is not in the fluff pulp it is disposed in the absorbent article such that it will be carried into contact with the chemiluminescent system (e.g., in the fluff pulp) upon insult.

Fluff Pulp

The fluff pulp of the fluff pulp composition can be formed from any pulp. In one embodiment, the fluff pulp is derived from a lignocellulosic fiber. In one embodiment, the fluff pulp is derived from a lignocellulosic fiber derived from wood. In one embodiment, the fluff pulp is derived from a lignocellulosic fiber derived from wood by chemical, mechanical, chemimechanical, or thermomechanical means. In one embodiment, the fluff pulp is derived from a cellulosic fiber derived from wood by chemical pulping. In one embodiment, the fluff pulp is derived from a cellulosic fiber derived from chemical pulping of wood either by alcohol pulping, organo-solve pulping, acid sulfite pulping, alkaline sulfite pulping, neutral sulfite pulping, alkaline peroxide pulping, Kraft pulping, Kraft-AQ pulping, polysulfide pulping, or polysulfide-AQ pulping. In one embodiment, the fluff pulp is derived from a cellulosic fiber derived from chemical pulping of wood by further removing lignin from the said pulp either by alcohol pulping, organo-solve pulping, acid sulfite pulping, alkaline sulfite pulping, neutral sulfite pulping, alkaline peroxide pulping, Kraft pulping, Kraft-AQ pulping, polysulfide pulping, or polysulfide-AQ pulping for the preparation of absorbent articles (fluff pulp). In one embodiment, the fluff pulp is derived from a cellulosic fluff pulp derived from Kraft pulping. In one embodiment, the fluff pulp is derived from a cellulosic bleached fluff pulp derived from Kraft pulping. In one embodiment, the fluff pulp is derived from a cellulosic bleached fluff pulp derived from Kraft pulping of softwoods. In one embodiment, the fluff pulp is derived from a cellulosic bleached fluff pulp derived from Kraft pulping of Southern softwoods. In one embodiment, the fluff pulp is derived from a cellulosic bleached fluff pulp derived from Kraft pulping of Southern pine. In one embodiment, the fluff pulp is derived from a Southern softwood. In one embodiment, the fluff pulp is derived from Southern pine.

The fluff pulp composition can be produced from pulp in any form, such as a wet-laid sheet which is dried to achieve a moisture content ranging from 6% to 11%.

In another aspect, methods of preparing the fluff pulp composition are provided. The fluff pulp composition is prepared by incorporating the chemiluminescent system into the fluff pulp. This can be accomplished using various methods that allow the fluff pulp to be treated with one or more components of the chemiluminescent system. One challenge in the chemical treatment of fluff pulp is to maintain the chemicals in a state in which the intended chemiluminescent reaction is not prematurely triggered, for example, before the treated fluff pulp is incorporated into an absorbent article that is then subjected to a liquid insult. For a wet end application, the chemicals typically cannot be comingled with water and be applied together. Accordingly, in an illustrative example, either the luciferase or luciferin may be microencapsulated and introduced during the wet-laying process, with the non-encapsulated component applied to the sheet in a non-aqueous environment by standard methods such as coating, dipping or spraying or printing (or combination thereof), prior to the air-laid operation during absorbent article manufacture. In another illustrative example, a two sheet system, one containing luciferase and the other containing luciferin, may be made and processed further before the air-laid operation during absorbent article manufacture. In yet other examples, one of the chemicals maybe added during the wet-laying process and the other during the subsequent processing of the pulp; or the two components may be added to the pulp during or prior to the air-laid process, such as by rinsing and/or spraying the pulp in fluffed form with non-aqueous solutions of the respective components.

The formation of a fluff pulp composition in accordance with the disclosed embodiments is described in detail in the Examples.

Absorbent Articles

In one embodiment, the fluff pulp composition can be incorporated into absorbent articles. Representative absorbent articles include child diapers, adult diapers, adult incontinence products, feminine hygiene products, absorbent underpads, and wound care dressing articles. For example, the fluff pulp composition may be incorporated into one or more absorbent layers or portions of an absorbent article.

In another aspect, an absorbent article is provided. In one embodiment, the absorbent article includes a top sheet that is liquid permeable, a back sheet that is liquid impermeable, fluff pulp disposed between the top sheet and the back sheet, and a chemiluminescent system configured to produce visible light upon contact with an aqueous system.

Figure 4A:
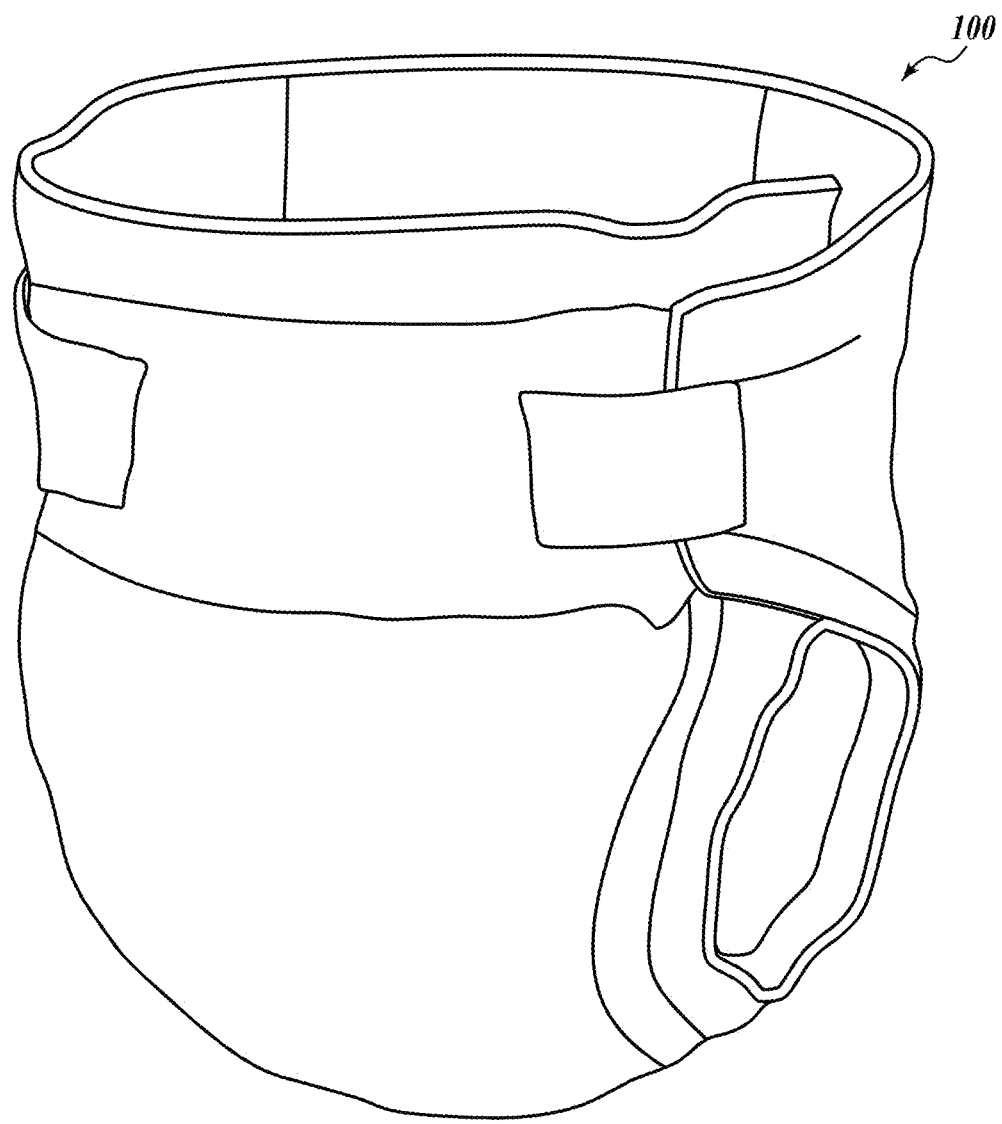
FIGS. 4A-4D illustrate a non-limiting representative example of an absorbent article (in the form of a diaper) in accordance with embodiments disclosed herein.
Figure 4B:
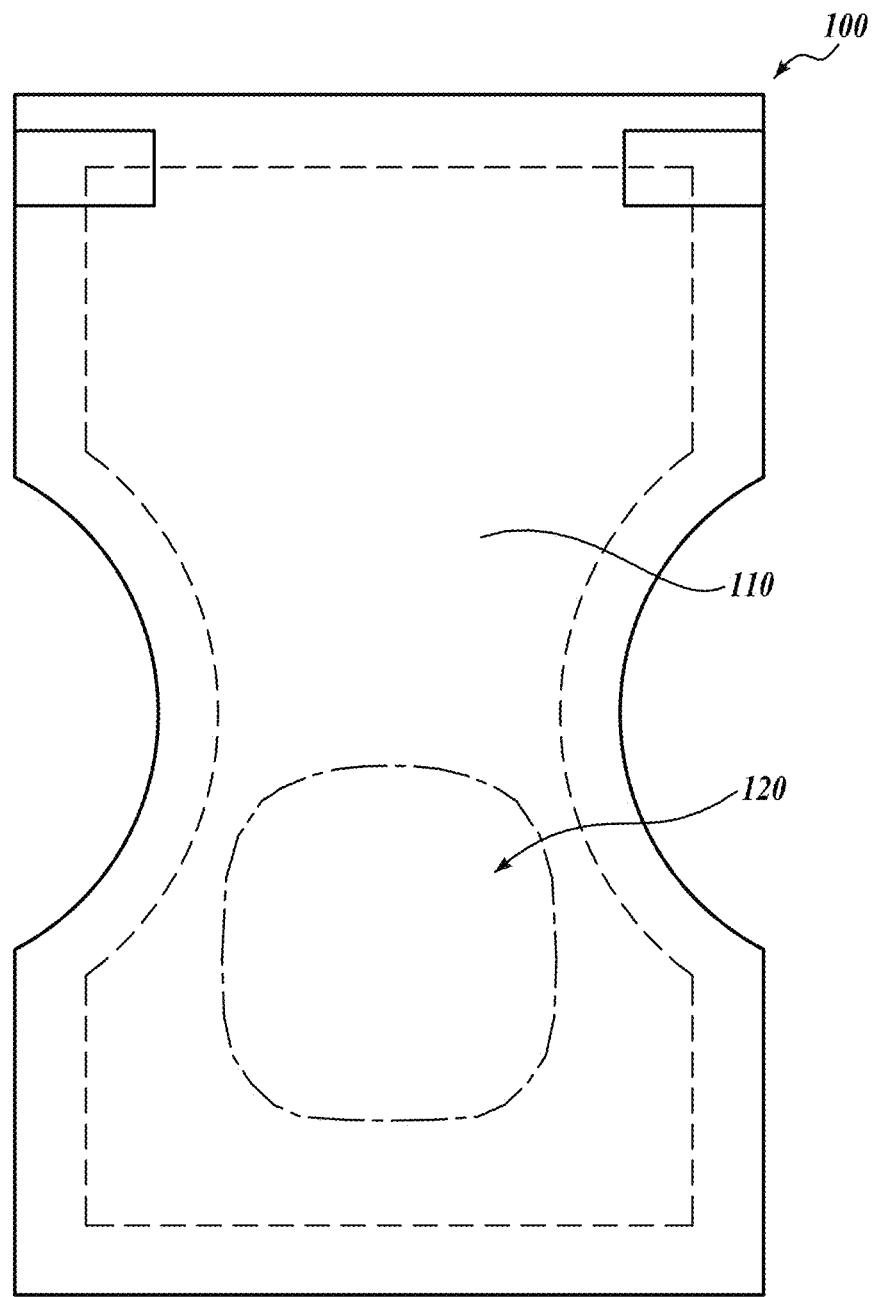
Figure 4C:
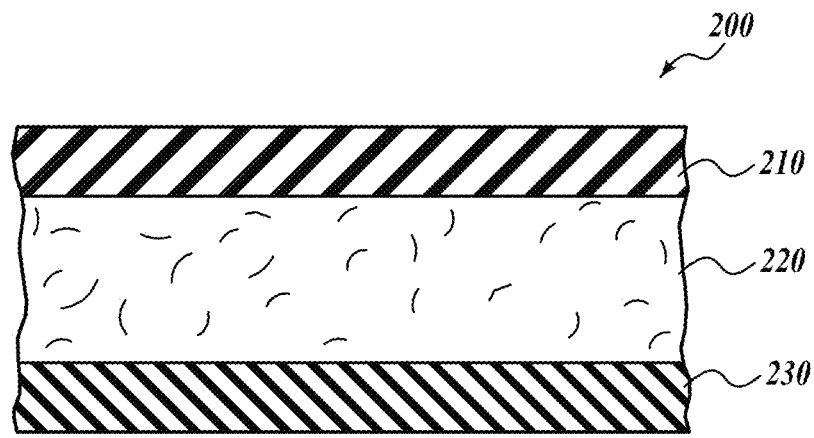

A representative absorbent article is illustrated in FIG. 4A as a diaper 100. However, the following description is equally applicable to all types of absorbent articles. Referring now to FIG. 4B, the diaper 100 is illustrated in flattened form. The diaper 100 includes a bulk absorbent region 110 and target region 120 in which an insult is expected FIG. 4C illustrates a cross-section 200 through the target region 120. In the cross-section 200 the diaper 100 includes a top sheet 210 that is liquid permeable, a back sheet 230 that is liquid impermeable, and an acquisition and distribution layer (ADL) 220. The ADL 220 is formed from or incorporates fluff pulp. The chemiluminescent system is incorporated into one or more of the top sheet 210, ADL 220, and back sheet 230 such that chemiluminescence is produced upon the target region 120 of diaper 100 receiving an insult.

Figure 4D:
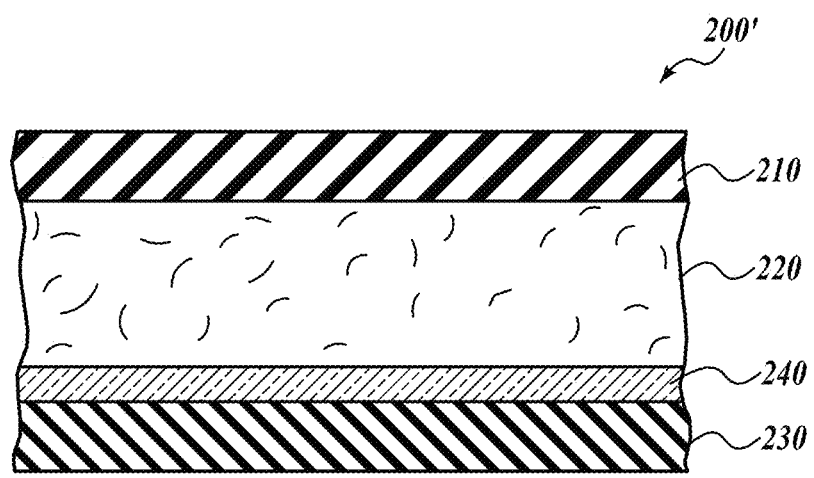

FIG. 4D illustrates a cross-section 200' of the diaper 100 similar to that shown in FIG. 4C, but with the addition of an absorbent core 240 (e.g., formed from a fibrous matrix with incorporated superabsorbent polymers). Once again, the chemiluminescent system is incorporated into one or more of the layers, top sheet 210, ADL 220, absorbent core 240, and back sheet 230. The absorbent core 240 may include the chemiluminescent system or components thereof.

The chemiluminescent system of the absorbent article is as described herein. However, it is evident that the chemiluminescent system need not be disposed, in whole or in part, within the fluff pulp.

In one embodiment, the chemiluminescent system comprises a luciferin and a luciferase. In one embodiment the luciferin and the luciferase are both disposed within the fluff pulp. In another embodiment, one of the luciferin and the luciferase is disposed within the fluff pulp and the other is disposed in a different layer (e.g., top sheet or ADL) of the absorbent product such that the two components are combined only when carried by a liquid insult (e.g., passing through the top sheet or ADL into the fluff pulp composition). In one embodiment the fluff pulp comprises a luciferin but not a luciferase. In one embodiment the fluff pulp comprises a luciferase but not a luciferin.

In yet another embodiment the chemiluminescent system is disposed on (for example, printed onto) the inner surface of the backsheet.

In one embodiment, one of the luciferin and the luciferase is disposed within the fluff pulp and the other is associated with the top sheet and configured to travel into the fluff pulp upon exposure to a liquid insult.

In one embodiment, the absorbent article further comprises a pH buffer, as disclosed herein. In one embodiment, the pH buffer is disposed within the fluff pulp.

In one embodiment, the absorbent article further comprises a photoluminescent compound, as disclosed herein. In one embodiment, the photoluminescent compound is disposed within the fluff pulp.

In one embodiment, the absorbent article further comprises a photoluminescent compound and a pH buffer, as disclosed herein. In one embodiment, the photoluminescent compound and the pH buffer are disposed within the fluff pulp.

In one embodiment, the pH buffer, the photoluminescent compound, the luciferin, and the luciferase are disposed within the fluff pulp In one embodiment, at least one of the pH buffer, the photoluminescent compound, the luciferin, and the luciferase are not disposed within the fluff pulp.

In one embodiment, the absorbent article further includes a superabsorbent polymer (SAP), such as incorporated in the absorbent core. In such an embodiment, at least one component of the chemiluminescent system may be disposed in the SAP, such that the chemiluminescence is generated upon the fluid from an insult traveling to the absorbent core.

In one embodiment the chemiluminescent system is contained entirely within an absorbent core of the absorbent article. As the absorbent core is almost always a multi-component system there exist more than one approach to incorporate the chemiluminescent system into the absorbent core. For instance the fluff pulp fibers could be the carrier of the chemiluminescent system. Alternatively, the chemiluminescent system could be contained within superabsorbent particles incorporated into the absorbent article.

Furthermore, if only a portion of the SAP particles or fibers contained the chemiluminescent system chemistry, a desired pattern, such as an aesthetically pleasing pattern, can be achieved.

The chemiluminescent system can be added to the fluff pulp fibers at the time of manufacture or during an upstream process entirely separated from final product assembly. As noted above, for example, the chemiluminescent system may be sprayed onto or otherwise incorporated into a fluff pulp sheet prior to hammermilling.

In another aspect, methods of manufacturing absorbent articles are also provided. Absorbent articles are manufactured according to general techniques known to those of skill in the art that allow the incorporation of the chemiluminescent system to be incorporated into the absorbent article in the manner disclosed herein.

The following examples are intended to be illustrative, not limiting.

EXAMPLES

The following paragraphs provide a description of illustrative manners in which fluff pulp compositions having an incorporated chemiluminescent system are manufactured and tested. Comparative testing against fluorescent-only wetness indicators is also described. The results illustrate the benefits of the chemiluminescent system for detecting wetness in the dark. The chemiluminescence can be seen through the absorbent article into which it is incorporated, as well as through clothing. The comparative fluorescent-only system requires an additional excitation light source and will not provide an indication through clothing.

Turning now to the illustrative samples, a Southern softwood pulp fiber, for example, PW 416 available from Weyerhaeuser (Federal Way, Wash.) in sheet form, was fluffed. The average bulk density of the pulp was measured to be 0.522 g/cc.

To 1000 ml of methanol (laboratory reagent, ≥99.6% purity, CAS 179957), 0.1 g to 1 g of L-ascorbic acid (ACS Reagent≥99.0% purity, CAS 255564) was added with a moderate to vigorous stirring until a supernatant solution was obtained. The supernatant solution was decanted of the undissolved ascorbic acid salt and a clear ascorbic acid in alcohol solution was obtained. The solution was divided into batches of 100 cc and used for different treatments. To the ascorbic acid in methanol solution, anywhere from 5 mg to 20 mg coelenterazine (93% purity) was added and stirred to complete dissolution.

The fluffed fiber (in about 1000 g portions) was rinsed in the coelenterazine solution, squeezed out of the solution and vacuum dried to recover the alcohol. Applied to the dried fluff pulp was either *Renilla* luciferase, *Gaussia* luciferase, or a 50:50 mixture of *Renilla* and *Gaussia* Luciferase proteins (at 15 to 20% purity for the luciferase). The ratio of luciferase to luciferin was set forth as 10 mg to 20 mg of luciferase to 1 mg of luciferin. A similar procedure was followed for the fluorescent agent, for example, Green Fluorescent Protein (GFP) either as a standalone treatment or in combination with the bioluminescence agents.

Absorbent core material was prepared by placing 7 g of the treated fluff fiber and an equal amount of luciferin-luciferase treated SAP (7 g) and untreated SAP in a 6" air laid former. Baby diapers were produced using the absorbent cores containing luciferin-luciferase treated SAP and fluff pulp and luciferin-luciferase treated fluff but untreated SAP as one component of the baby diaper. The diapers were wetted with 100 ml of saline solution (to simulate wetting of the diaper with urine) and the bioluminescence effect of wetting was visually observed under nocturnal light (dark) conditions. As seen in FIG. 5, the bioluminescent system effectively indicates the wetness of the diaper under night time conditions, through a lightweight cotton fabric. The intensity of the light was observed to be well maintained and sufficient for detection ever under cover and in darkness.

It was observed that higher amounts of luciferase tend to increase the intensity, but not the duration, of the chemiluminescence, and lower amounts of luciferase tend to increase the duration of the effect, but not the intensity.

Other diaper components (eg, the ADL or a portion thereof, the top/inner layer of the back sheet (facing the absorbent core), the SAP used in the absorbent core, etc.) were also subjected to the treatment described. In the case of the back sheet, instead of rinsing the entire back sheet, a 1" width thin layer coating of luciferin-luciferase with and without a photoluminescent material was applied and the layer consumed almost 1/10th of the material needed. All examples functioned similarly to the absorbent core samples to produce chemiluminescent wetness detection in the diapers.

Figure 6:
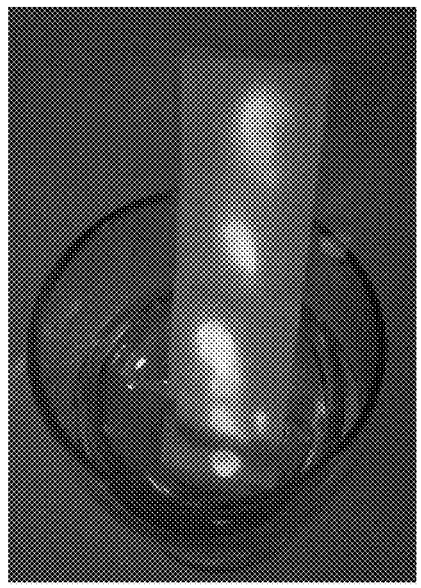

FIG. 6 illustrates the incorporation of a chemiluminescent system in accordance with the present disclosure into a dried wet laid-pulp sheet, and shows the chemiluminescence triggered by capillary rise of fluid into the sheet.

Figure 7:
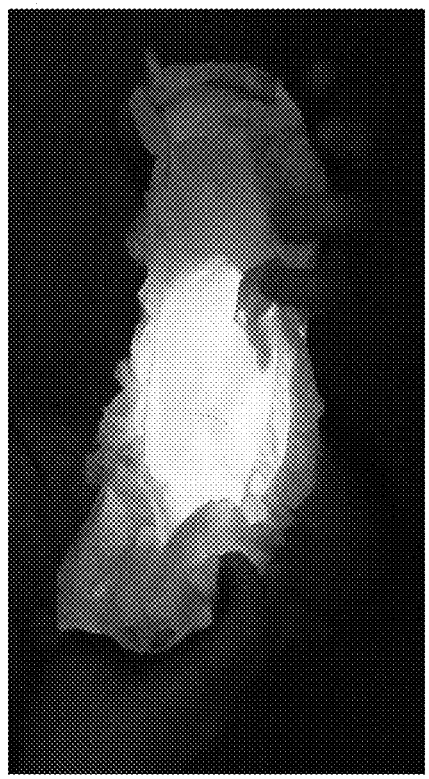
Figure 8:
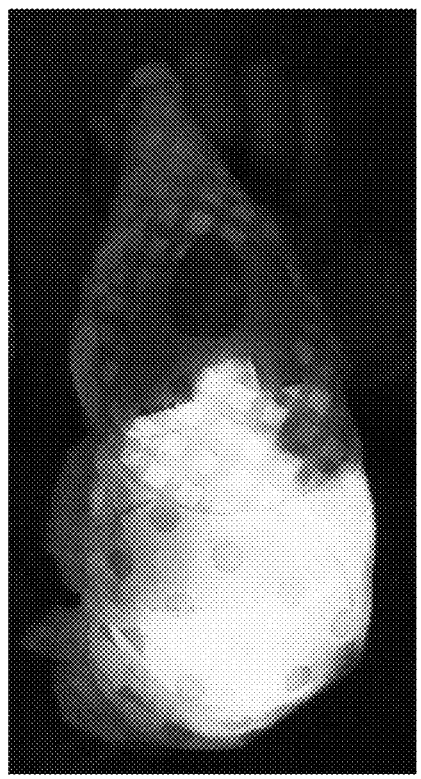

FIGS. 7 and 8 illustrate the intensity of the emitted visible light in an exemplary baby diaper after wetting.

Figure 9A:
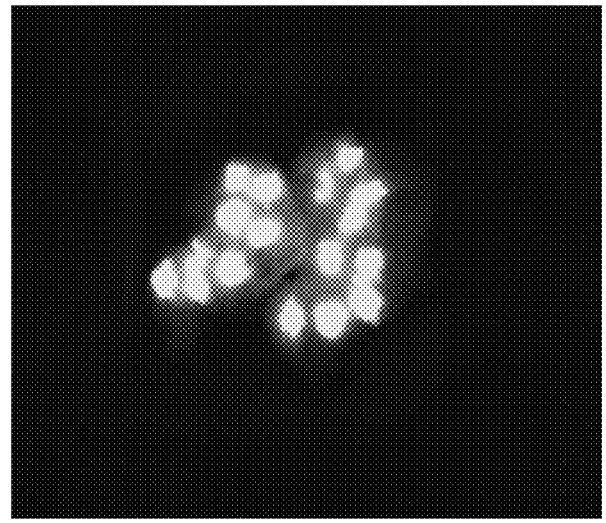
FIGS. 9A and 9B photographically depict comparative absorbent articles.
Figure 9B:
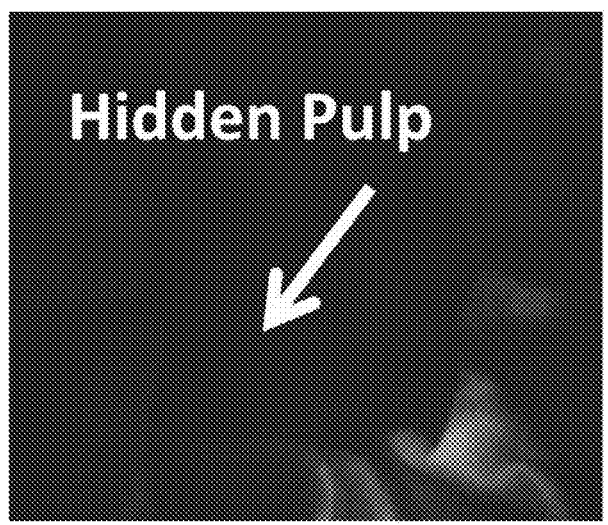

As a comparative example, FIG. 9A demonstrates the luminescence of pulp treated with a fluorescent mixture of Tinopal (Elcowhite TS from Greenville Colorants, Jersey City, N.J.) and rhodamine (Greenville Colorants) in a polyvinyl alcohol base (Sigma-Aldrich, St. Louis, Mo.), when excited by UV light in darkness in the absence of any bioluminescent chemical. FIG. 9B is the same as FIG. 9A, but with the pulp covered by a light weight cotton cloth similar to that covering the example of FIG. 5 and placed under UV light. In FIG. 9B the pulp is not visible, demonstrating the lack of detection of light under cover. This is because in order for the UV light to excite the fluorescent chemistry it must first pass through the cotton cloth. Accordingly, if the external light source is blocked the fluorescent agent cannot be excited and emit light. Because babies and adult patients typically either wear garments over their diapers and adult incontinent products and/or use covers while sleeping, these materials will block the light source required for excitation of the fluorescent chemical and limits its use as a nocturnal detection tool. In addition, the functionality of fluorescent agents is further frustrated because many household detergents contain optical brighteners to improve the whiteness of fabrics, and these optical brighteners absorb UV light, thereby depriving fluorescent chemicals the opportunity to excite and emit visible light when the diapers or adult incontinent products are worn or used under garments or other covers. Moreover, of course, light fluoresced by the diminished UV light must make the return journey through the cloth to be visible.

Chemiluminescence requires no such conditions. Furthermore, in the case of a combination of bioluminescence and fluorescence chemistry as disclosed in certain embodiments, the light source to trigger the excitation of the fluorescent chemical is internally provided by bioluminescence in optical communication with the fluorescent chemical. In this case, even if an external light source is not available, or completely blocked, the fluorescent chemistry would still function because of the presence of bioluminescence.

While illustrative embodiments have been illustrated and described, it will be appreciated that various changes can be made therein without departing from the spirit and scope of the invention.

The embodiments of the invention in which an exclusive property or privilege is claimed are defined as follows:

1. A fluff pulp composition, comprising fluff pulp and a chemiluminescent system, wherein the chemiluminescent system comprises at least a luciferase having a concentration of 0.1% to 20%, by weight of the fluff pulp, and wherein the chemiluminescent system is configured to produce visible light upon contact with an aqueous system and a luciferin.

2. The fluff pulp composition of claim 1, wherein the fluff pulp composition further comprises the luciferin.

3. The fluff pulp composition of claim 2, wherein the luciferin is selected from the group consisting of coelenterazine, dinoflagellate luciferin, bacterial luciferin, fungal luciferin, firefly luciferin, and vargulin.

4. The fluff pulp composition of claim 2, wherein the luciferin has a concentration of 0.01% to 2%, by weight of the fluff pulp.

5. The fluff pulp composition of claim 2, wherein the chemiluminescent system comprises coelenterazine as the luciferin and *Gaussia* or *Renilla* luciferase.

6. The fluff pulp composition of claim 1, wherein the luciferase is selected from the group consisting of *Gaussia* luciferase, *Renilla* luciferase, dinoflagellate luciferase, firefly luciferase, fungal luciferase, bacterial luciferase, and vargula luciferase.

7. The fluff pulp composition of claim 1, further comprising a pH buffer configured to provide buffering of the aqueous system between a pH of 4.0 to 8.5.

8. The fluff pulp composition of claim 7, wherein the pH buffer is selected from the group consisting of sodium bicarbonate, sodium acetate, sodium citrate, sodium lactate, sodium lactate citrate, sodium borate, calcium acetate, calcium citrate, calcium bromide, calcium gluconate, calcium lactate, calcium lactate malate, calcium carbonate, calcium bicarbonate, potassium dihydrogen phosphate, and combinations thereof.

9. The fluff pulp composition of claim 7, wherein the pH buffer is configured to extend a duration of the visible light upon contact with the aqueous system.

10. The fluff pulp composition of claim 1, further comprising a photoluminescent compound having a photoluminescent absorption wavelength range that overlaps with a chemiluminescent emission wavelength range of the chemiluminescent system, wherein the photoluminescent compound has a photoluminescent emission wavelength range that is different from the chemiluminescent emission wavelength range.

11. The fluff pulp composition of claim 10, wherein the photoluminescent compound is selected from the group consisting of a fluorescent compound and a phosphorescent compound.

12. The fluff pulp composition of claim 10, wherein the photoluminescent compound is present in an amount of 0.01% to 2% by weight of the fluff pulp.

13. The fluff pulp composition of claim 1, wherein the visible light has a duration of 0.5 to 6 hours.

14. The fluff pulp composition of claim 1, wherein the fluff pulp composition is in the form of a fluff pulp sheet.

15. An absorbent article, comprising:
a top sheet that is liquid permeable;
a back sheet that is liquid impermeable;
fluff pulp disposed between the top sheet and the back sheet; and
a chemiluminescent system configured to produce visible light upon contact with an aqueous system;
wherein the chemiluminescent system comprises a luciferin and a luciferase; and
wherein the luciferin is present in a concentration of 0.01% to 2%, by weight of the fluff pulp.

16. The absorbent article of claim 15, wherein the luciferin and the luciferase are both disposed within the fluff pulp.

17. The absorbent article of claim 15, wherein one of the luciferin or the luciferase is disposed within the fluff pulp and the other is associated with the top sheet and configured to travel into the fluff pulp upon exposure to a liquid insult.

18. The absorbent article of claim 15, further comprising a pH buffer configured to provide buffering of the aqueous system between a pH of 4.0 to 8.5.

19. The absorbent article of claim 15, further comprising a photoluminescent compound having a photoluminescent absorption wavelength range that overlaps with a chemiluminescent emission wavelength range of the chemiluminescent system, wherein the photoluminescent compound has a photoluminescent emission wavelength range that is different from the chemiluminescent emission wavelength range.

20. The absorbent article of claim 15, further comprising a superabsorbent polymer.

21. A fluff pulp composition, comprising fluff pulp and a chemiluminescent system, wherein the chemiluminescent system comprises at least a luciferin having a concentration of 0.01% to 2%, by weight of the fluff pulp, and wherein the chemiluminescent system is configured to produce visible light upon contact with an aqueous system and a luciferase.

22. The fluff pulp composition of claim 21, wherein the luciferin is selected from the group consisting of coelenterazine, dinoflagellate luciferin, bacterial luciferin, fungal luciferin, firefly luciferin, and vargulin.

23. The fluff pulp composition of claim 21, wherein the fluff pulp composition is in the form of a fluff pulp sheet.

24. A fluff pulp sheet comprising fluff pulp fibers treated with a chemiluminescent system, wherein the chemiluminescent system comprises at least a first component selected from a luciferin and a luciferase, and wherein the chemiluminescent system is configured to produce visible light upon contact of the treated fluff pulp fibers with an aqueous system and a second component selected from the other of the luciferin and the luciferase.

25. The fluff pulp sheet of claim 24, having a luciferin as the first component with a concentration of 0.01% to 2%, by weight of the fluff pulp fibers.

26. The fluff pulp sheet of claim 24, having a luciferase as the first component with a concentration of 0.1% to 20%, by weight of the fluff pulp fibers.

27. The fluff pulp sheet of claim 24, further comprising a pH buffer configured to provide buffering of the aqueous system between a pH of 4.0 to 8.5.

28. The fluff pulp sheet of claim 24, further comprising a photoluminescent compound having a photoluminescent absorption wavelength range that overlaps with a chemiluminescent emission wavelength range of the chemiluminescent system.

29. The fluff pulp sheet of claim 24, wherein the chemiluminescent system comprises coelenterazine as the second component and *Gaussia* or *Renilla* luciferase as the first component.

30. An absorbent article, comprising:
a top sheet that is liquid permeable;
a back sheet that is liquid impermeable and having an inner surface that faces the top sheet;
fluff pulp disposed between the top sheet and the back sheet; and
a chemiluminescent system, comprising at least a first component selected from a luciferin and a luciferase;
wherein at least one component of the chemiluminescent system is disposed on the inner surface of the back sheet, and wherein the chemiluminescent system is configured to produce visible light upon contact with an aqueous system and a second component selected from the other of the luciferin and the luciferase.

31. The absorbent article of claim 30, wherein at least the first component of the chemiluminescent system is printed on the inner surface of the back sheet.

32. The absorbent article of claim 31, wherein the chemiluminescent system includes both a luciferin and a luciferase, and wherein both the luciferin and the luciferase are printed on the inner surface of the back sheet.

33. A method of producing an absorbent article for detection of an aqueous insult, the method comprising:
applying a chemiluminescent system, comprising at least a first component selected from a luciferin and a luciferase, to a structural component for an absorbent article selected from the group consisting of a liquid-permeable top sheet, a liquid-impermeable back sheet, fluff pulp, and superabsorbent polymer;
wherein a sufficient quantity of the chemiluminescent system remains on the structural component article to react with an aqueous system to produce visible light in the presence of an aqueous system and a second component selected from the other of the luciferin and the luciferase; and
producing an absorbent article using the structural component.

34. The method of claim 33, wherein the absorbent article is a diaper.

35. The method of claim 33, wherein the applying includes applying at least the first component to the fluff pulp, and applying the second component to the liquid-impermeable back sheet.

36. The method of claim 33, wherein the applying includes applying both a luciferin and a luciferase to the liquid-impermeable back sheet.

37. A liquid-impermeable back sheet, the back sheet comprising opposed surfaces and a chemiluminescent system disposed on at least one of the opposed surfaces, wherein the chemiluminescent system comprises at least a first component selected from a luciferin and a luciferase, and wherein the chemiluminescent system is configured to produce visible light upon contact with an aqueous system and a second component selected from the other of the luciferin and the luciferase.

38. The liquid-impermeable back sheet of claim 37, wherein at least the first component of the chemiluminescent system is printed on the at least one surface.

39. The liquid-impermeable back sheet of claim 37, wherein the chemiluminescent system includes a luciferin and a luciferase, and wherein the luciferin and the luciferase are disposed on the at least one surface.

40. An absorbent article, comprising:
a top sheet that is liquid permeable;
a back sheet that is liquid impermeable and having an inner surface that faces the top sheet;
an absorbent core disposed between the top sheet and the back sheet; and
superabsorbent polymer disposed between the top sheet and the back sheet;
wherein at least some of the superabsorbent polymer is treated with a chemiluminescent system, wherein the chemiluminescent system comprises at least one component selected from a luciferin and a luciferase, and wherein the chemiluminescent system is configured to produce visible light upon contact with an aqueous system and the other of the luciferin and the luciferase.

41. A superabsorbent polymer composition, comprising superabsorbent polymer particles treated with a chemiluminescent system, wherein the chemiluminescent system comprises at least one component selected from a luciferin and a luciferase, and wherein the chemiluminescent system is configured to produce visible light upon contact of the treated superabsorbent polymer particles with an aqueous system and the other of the luciferin and the luciferase.

42. A method of producing a treated fluff pulp composition, the method comprising:
forming a fluff pulp sheet from pulp fibers in an aqueous slurry, using a wet-laying process;
treating one or more the pulp fibers and the fluff pulp sheet formed therefrom with a chemiluminescent system that includes a luciferin and a luciferase that are configured to react with each other in the presence of an aqueous system to produce visible light; and
wherein sufficient quantities of unreacted luciferin and luciferase remain on the pulp fibers of the treated fluff pulp sheet to react with an aqueous system to produce visible light.

43. The method of claim 42, wherein the treating step is performed during a wet-laying process prior to drying, and wherein the treating step includes adding one of the luciferin and the luciferase in microencapsulated form to the pulp fibers.

44. The method of claim 43,
wherein the method further includes, subsequent to the forming step, adding the other of the luciferin and the luciferase to the treated fluff pulp sheet.

45. The method of claim 44, wherein adding the other of the luciferin and the luciferase in a non-aqueous environment to the treated fluff pulp sheet.

46. The method of claim 42, wherein the treating step is performed during a wet-laying process prior to drying, and wherein the treating step includes adding the luciferin and the luciferase in a non-aqueous solution to the pulp fibers.

* * * * *

UNITED STATES PATENT AND TRADEMARK OFFICE
CERTIFICATE OF CORRECTION

Page 1 of 1

PATENT NO. : 10,273,463 B2
APPLICATION NO. : 14/516255
DATED : April 30, 2019
INVENTOR(S) : B. A. Petersen et al.

It is certified that error appears in the above-identified patent and that said Letters Patent is hereby corrected as shown below:

In the Claims

| Column | Line | Error |
|---|---|---|
| 20 (Claim 42, Line 5) | 3 | "one or more the pulp" should read --one or more of the pulp-- |

Signed and Sealed this
Twelfth Day of November, 2019

Andrei Iancu
*Director of the United States Patent and Trademark Office*